United States Patent [19]

Inouye et al.

[11] 4,209,509

[45] Jun. 24, 1980

[54] SUBSTANCE SF-1739 DERIVATIVES, PROCESS FOR PREPARING THE SAME AND ANTIBACTERIAL COMPOSITIONS CONTAINING THE SAME

[75] Inventors: Shigeharu Inouye; Takashi Shomura, both of Yokohama; Michio Kojima, Tokyo; Takashi Hisamatsu, Yokohama, all of Japan

[73] Assignee: Meiji Seika Kaisha Ltd., Tokyo, Japan

[21] Appl. No.: 8,406

[22] Filed: Feb. 1, 1979

[30] Foreign Application Priority Data

Feb. 8, 1978 [JP] Japan .................................. 53-13122
Aug. 16, 1978 [JP] Japan .................................. 53-99144
Sep. 4, 1978 [JP] Japan .................................. 53-107492

[51] Int. Cl.$^2$ ............................................. A61K 35/00
[52] U.S. Cl. .................................... 424/119; 424/120; 424/121; 424/122; 435/169

[58] Field of Search ............... 424/119, 120, 121, 122; 198/80; 435/169

[56] References Cited

PUBLICATIONS

Chemical Abstracts, 86:119253a, (1977).

*Primary Examiner*—Jerome D. Goldberg
*Attorney, Agent, or Firm*—Frishauf, Holtz, Goodman & Woodward

[57] ABSTRACT

Substance SF-1739 derivatives, Substance SF-1739 HP, Substance SF-1739 HP-C, Substance SF-1739 HP-F, Substance SF-1739 HP-3 and Substance SF-1739 HP-5, the physico-chemical properties of which derivatives are described in the specification; processes for preparing such SF-1739 derivatives; and antimicrobial compositions containing at least one of the said Substance SF-1739 derivatives.

11 Claims, 16 Drawing Figures

SUBSTANCE SF-1739 DERIVATIVES, PROCESS FOR PREPARING THE SAME AND ANTIBACTERIAL COMPOSITIONS CONTAINING THE SAME

This invention relates to a new group of substance SF-1739 derivatives, processes for preparing the same and antibacterial and antitumor compositions containing as an active ingredient at least one of the same.

More particularly, it is concerned with new and useful substance SF-1739 derivatives, namely Substance SF-1739 HP, Substance SF-1739 HP-C, Substance SF-1739 HP-F, Substance SF-1739 HP-3 and Substance SF-1739 HP-5, processes for preparing such SF-1739 derivatives, as well as antimicrobial and antitumor compositions containing as an active ingredient at least one of the said substance SF-1739 derivatives.

In the prior art, it was disclosed in Japanese Published Unexamined Patent Application No. 125798/1976 (filed by Meiji Seika Kaisha Ltd., Japan, on Apr. 24, 1975 as Application No. 49131/1975) that an antibiotic substance SF-1739 can be produced by cultivation of Streptomyces griseoplanus strain SF-1739. Also, according to the report in the Annual Report of Meiji Seika Laboratories, Vol. 16, page 20, the substance SF-1739 is a yellow diacid base with an unidentified chemical structure and physico-chemical and biological properties thereof are discussed detailedly in that report. Further, it was known that the substance SF-1739 is extremely unstable under an alkaline condition and even its free base is decomposed into various fractions having no antibacterial activities after standing in a dry state for several days, whereas it is very stable under an acidic condition.

We have further studied stability of the substance SF-1739 under an acidic condition and, as a result, it has been found that a new Substance SF-1739 HP can be obtained by treatment of the substance SF-1739 with a strong acid and the new substance can exhibit potent antibacterial and antitumor activities.

And further, in view of the fact that the new and useful Substance SF-1739 HP shows a considerably higher toxicity, we have made further studies on derivatives of the substance SF-1739 HP in order to reduce its toxicity and it has also been found that a new group of substance SF-1739 HP derivatives, namely Substance SF-1739 HP-C and Substance SF-1739 HP-F can be obtained by reaction of the substance SF-1739 HP with a cyanide or formamide and they can satisfactorily serve the purpose as intended.

On the other hand, we have studied other metabolites which may be produced in a cultured broth by cultivation of such actinomycetes as Streptomyces griseoplanus strain SF-1739 (Japanese Published Unexamined Patent Application No. 125798/1976). As a result, we have found that there is produced in a culture broth yellow metabolites which are definitely different from the substance SF-1739, although they have also Rf values and also that new antibiotic substances, namely Substance SF-1739 HP-3 and Substance SF-1739 HP-5 can be derived from the yellow metabolites by treatment with a strong acid.

It is, accordingly, a primary object of this invention to provide a new group of five antibiotic substances; Substance SF-1739 HP, Substance SF-1739 HP-C, Substance SF-1739 HP-F, Substance SF-1739 HP-3 and Substance SF-1739 HP-5.

Another object of this invention is to provide a process for preparing these antibiotic substances.

Still another object of this invention is to provide an antibacterial or antitumor composition containing as an active ingredient at least one of such substance SF-1739 derivatives.

According to one aspect of this invention, there are provided, as depicted above, five different derivatives of the substance SF-1739. Each of these derivatives and preparations will be more fully described hereinbelow.

I. Substance SF-1739 HP (1) Physico-chemical properties

Figure 1:
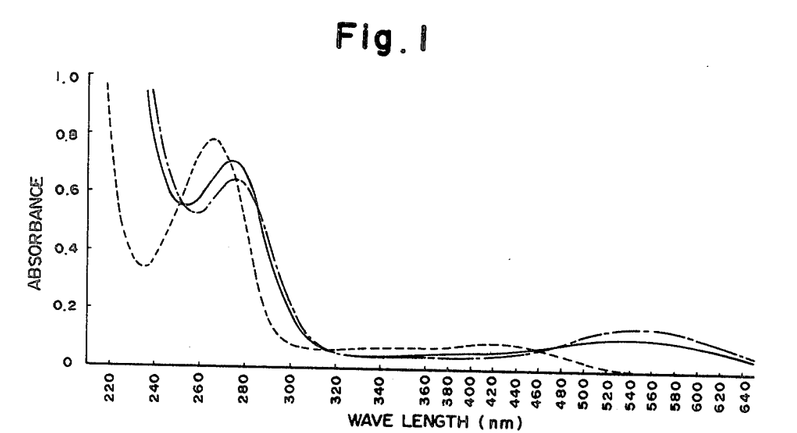
Figure 2:
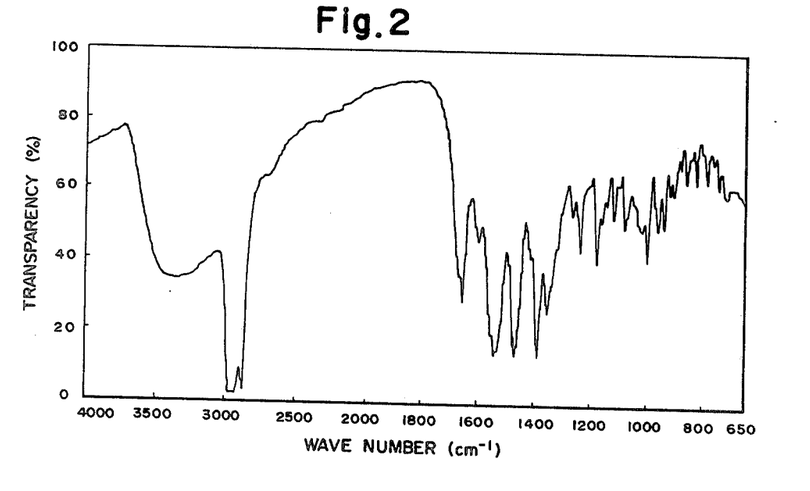
Figure 3:
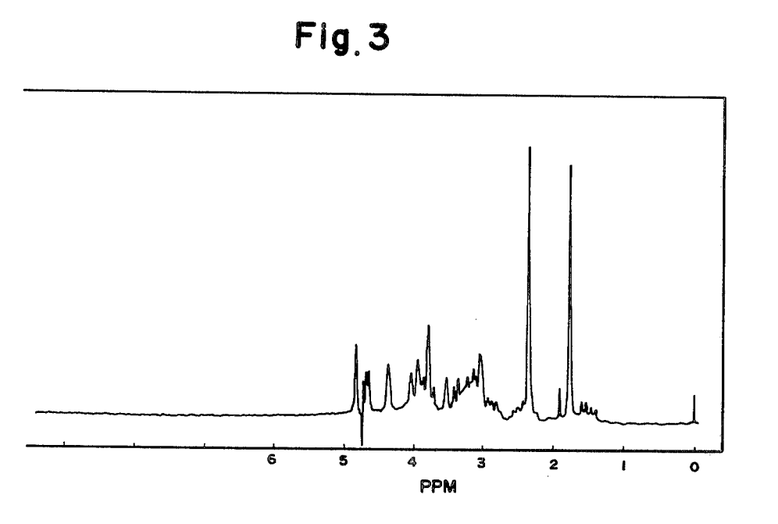
Figure 4:
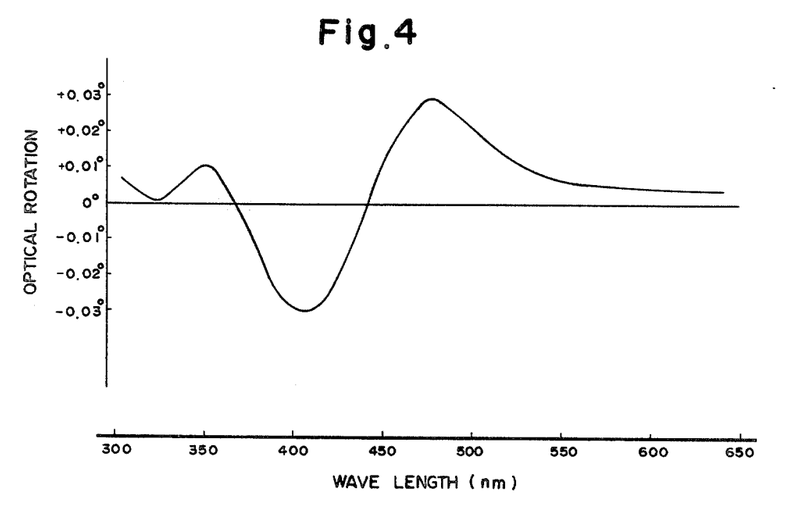

This substance has no definite melting point and melts with blackening over a wide range beginning at around 150°–180° C. It has an ultraviolet absorption spectrum, as shown in FIG. 1, in methanol [illustrated with a solid line (—) in FIG. 1] with three absorption maxima at 220 nm ($E_{1\,cm}^{1\%}=407$), 275 nm (132) and 535 nm (21), the one in 0.05 N HCl- 95% methanol [illustrated with a dotted line ( . . . . ) in FIG. 1], with two absorption maxima at 265 nm ($E_{1\,cm}^{1\%}=754$), 410 (16), and the one in 0.05 N NaOH- 95% methanol [illustrated with a chain line ( ) in FIG. 1] with absorption maxima at 221 nm ($E_{1\,cm}^{1\%}=440$), 277 (124), 345 (shoulder) and 540 (24). It shows an infrared absorption spectrum (in Nujol) as shown in FIG. 2 with characteristic absorption bands at 3350, 1655, 1600, 1540, 1355, 1265, 1235, 1180, 1120, 1080, 1020, 1000, 965, 945, 920, 910, 865, 830, 790 and 750 $cm^{-1}$ and a nuclear magnetic resonance spectrum (in $D_2O$) as shown in FIG. 3. Its mass spectrum shows peaks at m/e 412, 430, whereupon its molecular weight is estimated to be approximate to that of the substance SF-1739. It has the analytical composition: C, 62.19%, H, 6.95%; N, 8.50%; O, 22.36% (by difference). It shows a optical rotatory dispersion curve as shown in FIG. 4, from which its specific rotation $[\alpha]_{589}^{18}+70°$ is calculated (in 0.05% methanol). It is a blackish purple substance which is easily soluble in water and methanol, soluble in acetone and ethyl acetate and sparingly soluble in hexane. Its Rf values over a silica gel thin layer chromatography plate (available from E. Merck, West Germany) are 0.45 when developed with chloroform: methanol (9:1) and 0.23 when developed with n-butanol: methanol: 0.1 N HCl (4:2:1), while the corresponding values of the substance SF-1739 are 0.76 and 0.39, respectively. The stability of Substance SF-1739 HP is greatly improved as compared with that of the starting substance SF-1739 and stable under both acidic and alkaline conditions. For instance, even when left in 5 N HCl at room temperature overnight, it is completely stable, whereas the starting substance SF-1739 is substantially converted to Substance SF-1739 HP. Also, even when left in 0.1 N NaOH methanol at room temperature overnight, it does not show any significantly reduced antibacterial activity, whereas the starting substance SF-1739 is substantially inactivated.

(2) Preparation

This substance can be prepared from the substance SF-1739 by treatment with an acid. As the acid which may be employed for this treatment, there may be mentioned a mineral acid such as hydrochloric acid, hydrobromic acid, sulfuric acid and the like; and an organic acid such as trifluoroacetic acid methanesulfonic acid, trifluoromethanesulfonic acid and the like. Reaction parameters may vary depending upon the sort and concentration of an acid to be employed and the solvent to be used. In case of the mineral acid, the treatment is desirably effected under cooling or at room temperature for 1 day to 1 week when a higher concentration of 5 to 10 N is applied or at room temperature or higher for one to several days when a lower concentration of not more 5 N is applied. At an elevated temperature of above 80° C., by-products sometimes tend to be rather increased. The treatment may proceed rather rapidly in an aqueous solution, while it does more slowly in aqueous methanol. Conversion of the substance SF-1739 to Substance SF-1739 HP may take place at a pH below 3.

After completion of the treatment, Substance SF-1739 HP can be easily recovered from the reaction mixture by a conventional method, utilizing the above-recited physico-chemical properties of Substance SF-1739 HP. For instance, the reaction mixture can be neutralized with a base, e.g. sodium hydrogencarbonate, potassium carbonate and the like, concentrated to dryness. The residue is then extracted with methanol and is purified directly by a preparative silica gel thin layer chromatography. Alternatively, as less by-products are produced in this treatment, the reaction mixture can be concentrated, the residue dissolved in methanol, the resulting solution neutralized, and then passed through a column of Sephadex LH-20 (available from Pharmacia, Sweden), which can be subsequently developed with methanol or a mixed solvent of ethyl acetate and methanol to purify the desired product.

II. Substance SF-1739 HP-C and Substance SF-1739 HP-F

(II-a) Substance SF-1739 HP-C (1) Physico-chemical properties

Figure 5:
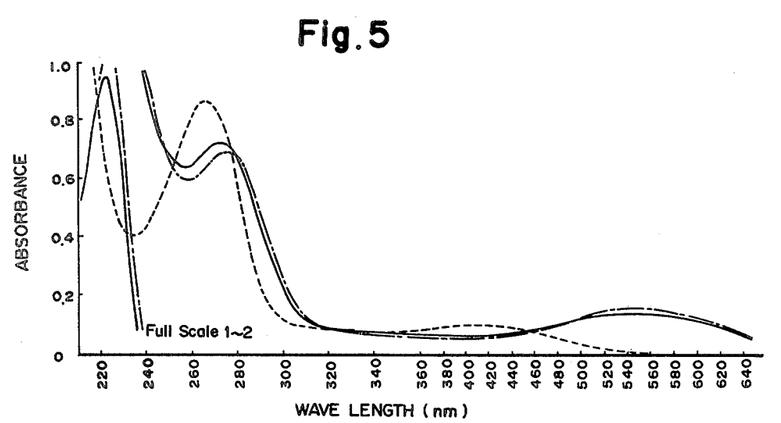
Figure 6:
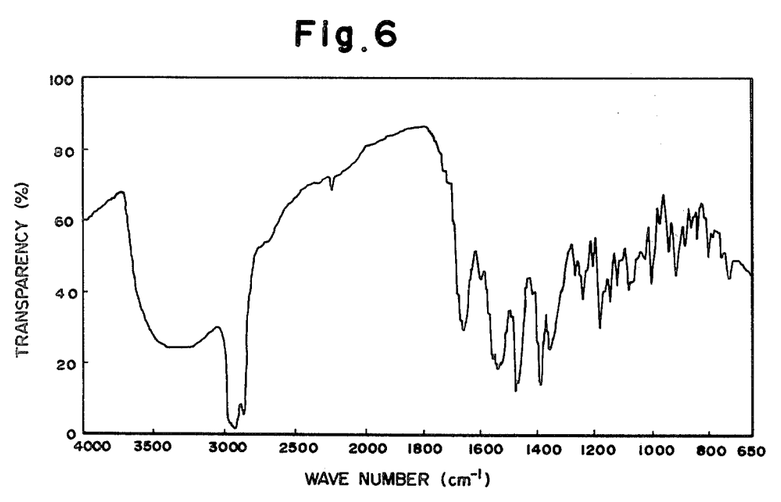
Figure 7:
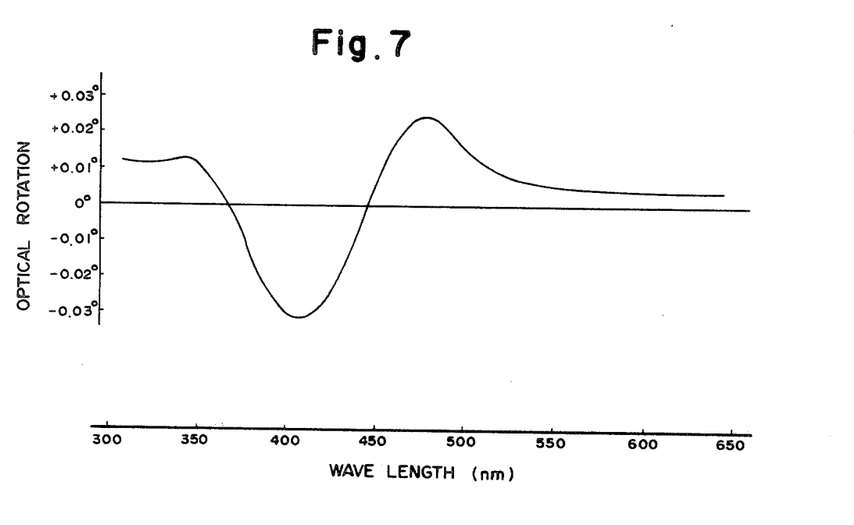
Figure 8:
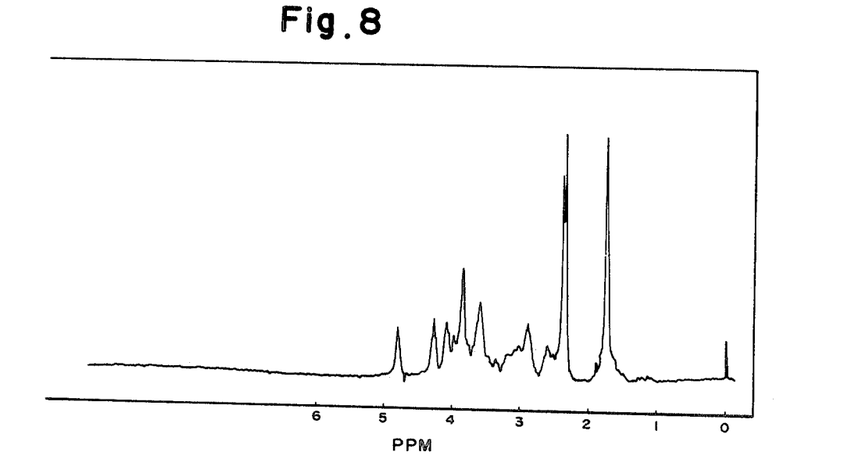

This substance has no definite melting point and melts with blackening over a wide range beginning at around 120°-150° C. It has an ultraviolet absorption spectrum, as shown in FIG. 5, in methanol [illustrated with a solid line in FIG. 5] with three absorption maxima at 222 nm ($E_1\ _{cm}^{1\%}=400$), 273 nm (146), and 540 nm (30), the one in 0.1 N HCl- 90% methanol [illustrated with a dotted line in FIG. 5] with absorption maxima at 204 nm, 266 nm ($E_1\ _{cm}^{1\%}=174$) and 410 nm (22) and the one in 0.1 N NaOH- 90% methanol [illustrated with a chain line in FIG. 5] with absorption maxima at 222 nm ($E_1\ _{cm}^{1\%}=422$), 275 nm (140) and 550 nm (32). It shows an infrared absorption spectrum (in Nujol) as shown in FIG. 6 with characteristic absorption bands at 3350, 1660, 1535, 1355, 1265, 1235, 1200, 1175, 1140, 1120, 1080, 1060, 1000, 940, 910, 880, 835 and 795 cm$^{-1}$; optical rotatory dispersion curve as shown in FIG. 7; and nuclear magnetic resonance spectrum (in D$_2$O) as shown in FIG. 8. It has the analytical composition: C, 59.58%; H, 6.14%; N, 12.63%; O, 21.65% (by difference). It is a blackish purple substance which is easily soluble in water and methanol, soluble in acetone and ethyl acetate and sparingly soluble in hexane. Its Rf values over a silica gel thin layer plate (available from E. Merck, West Germany) are 0.40 when developed with chloroform:methanol (9:1) and 0.70 when developed with ethyl acetate:methanol (3:2), while the corresponding values of Substance SF-1739 HP are 0.26 and 0.31, respectively. It is stable in dry state and in neutral, acidic and alkaline methanolic solution.

(II-b) Substance SF-1739 HP-F (1) Physico-chemical properties

Figure 9:
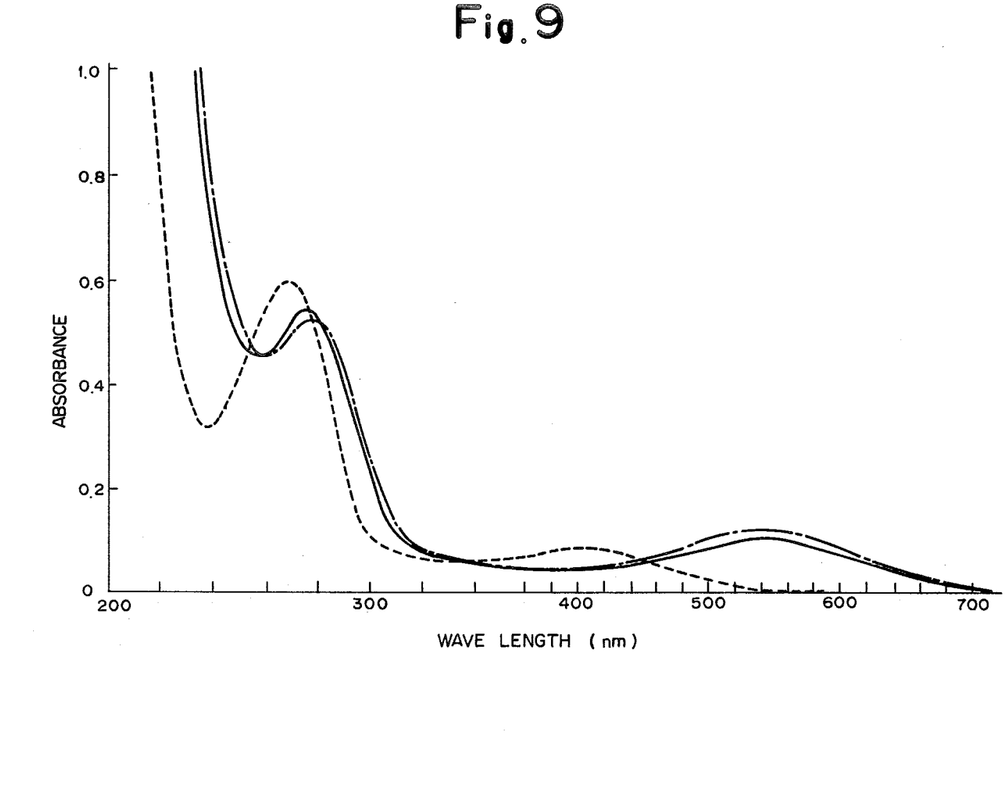
Figure 10:
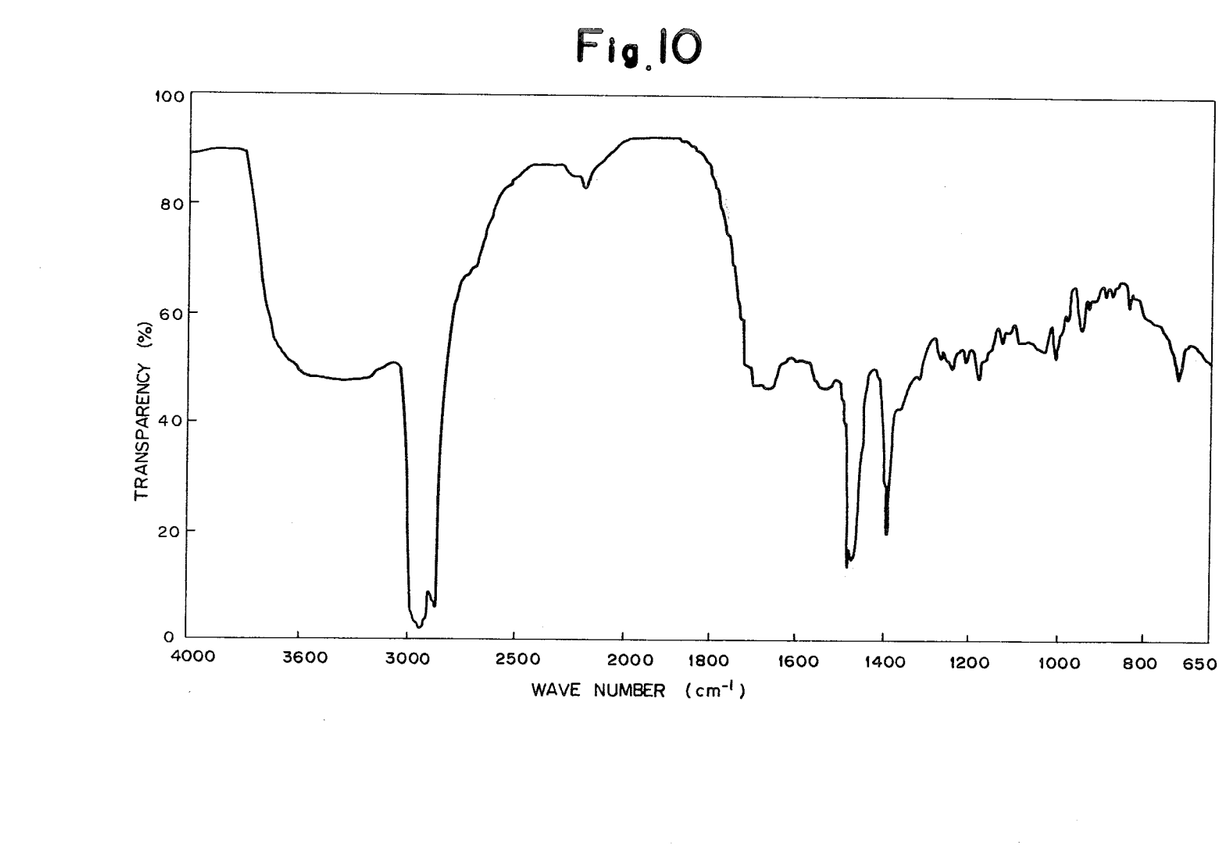

This substance has no definite melting point and melts with blackening over a wide range beginning at around 110°-140° C. It has an ultraviolet absorption spectrum, as shown in FIG. 9, in methanol [illustrated with a solid line in FIG. 9] with three absorption maxima at 220 nm, 275 nm ($E_1\ _{cm}^{1\%}=121$) and 540 nm (24), the one in 0.1 N HCl- 90% methanol [illustrated with a dotted line in FIG. 9] with absorption maxima at 205 nm, 268 nm ($E_1\ _{cm}^{1\%}=133$) and 405 nm (19) and the one in 0.1 N NaOH- 90% methanol [illustrated with a chain line in FIG. 9] at 221 nm, 277 nm ($E_1\ _{cm}^{1\%}=117$) and 540 nm (29). It shows an infrared absorption spectrum (in Nujol) as shown in FIG. 10 with characteristic absorption bands at 3300, 1660, 1530, 1350, 1310, 1265, 1235, 1205, 1175, 1125, 1085, 1025, 1000, 940, 920, 830 and 795 cm$^{-1}$. It has the analytical composition: C, 57.26%; H, 6.33%; N, 12.14%; O, 24.27% (by difference). It is a blackish purple substance which is easily soluble in water and methanol, soluble in acetone and ethyl acetate and sparingly soluble in hexane. Its Rf values over a silica gel thin layer plate (available from E. Merck, West Germany) are 0.28 when developed with chloroform:methanol (9:1) and 0.53 when developed with ethyl acetate:methanol (3:2), while the corresponding values of Substance SF-1739 HP are 0.26 and 0.31, respectively. It is stable in dry state and in neutral and alkaline methanolic but less stable in acidic methanol.

(II-c) Preparation of both Substances

Substance SF-1739 HP-C can be prepared from Substance SF-1739 HP, which is formed as in the above item I, (2), by reaction with a cyanide.

As the cyanide which may be employed, there may be mentioned, for example, an alkali metal, alkaline earth metal, metal or organic amine (including ammonia) salt of hydrocyanic acid such as sodium, potassium, lithium, magnesium or ammonium cyanide and so on; and a compound capable of producing a cyanide ion (CN$^-$) secondarily such as cyanogen bromide and so on.

On the other hand, Substance SF-1739 HP-F can be prepared from Substance SF-1739 HP by reaction with formamide.

In both cases, reaction may proceed rapidly under cooling or at room temperature and substantially completed in about 5 to 30 minutes. At an elevated temperature above room temperature, by-products sometimes tend to be increased. As the reaction solvent which may be used in each case, there may be mentioned, for example, water; an alcohol; dimethylformamide; a mixed solvent of a water-miscible organic solvent and water and the like. Besides, formamide may be used in an excess amount to act as both a reagent and a solvent for the preparation of Substance SF-1739 HP-F.

After completion of the reaction, the desired product may be easily recovered and purified by a conventional method, utilizing the above-recited physico-chemical properties of each Substance. For instance, the reaction mixture can be concentrated to dryness and the residue is extracted with methanol, and then the extract is purified directly by a preparative silica gel thin layer chromatography.

Alternatively, as less by-products in each reaction, the reaction mixture can be concentrated, the residue is dissolved in methanol and the resulting solution is then passed through a column of Sephadex LH-20 (available from Pharmacia, Sweden), which can be subsequently developed with methanol or a mixed solvent of ethyl acetate and methanol to purify the desired product.

III. Substance SF-1739 HP-5 and Substance SF-1739-HP-3

(III-a) Substance SF-1739-HP-5

(1) Physico-chemical properties

Figure 11:
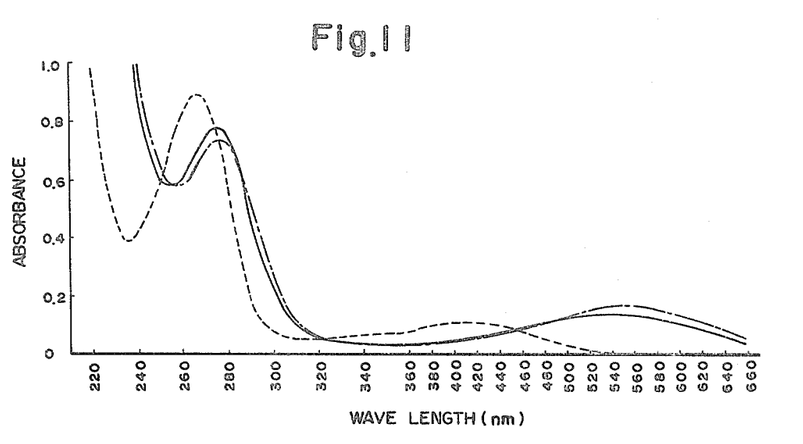
Figure 12:
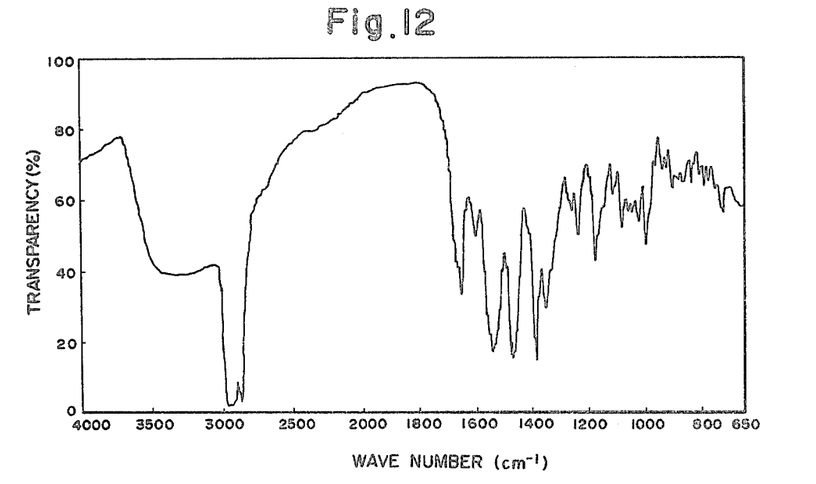
Figure 13:
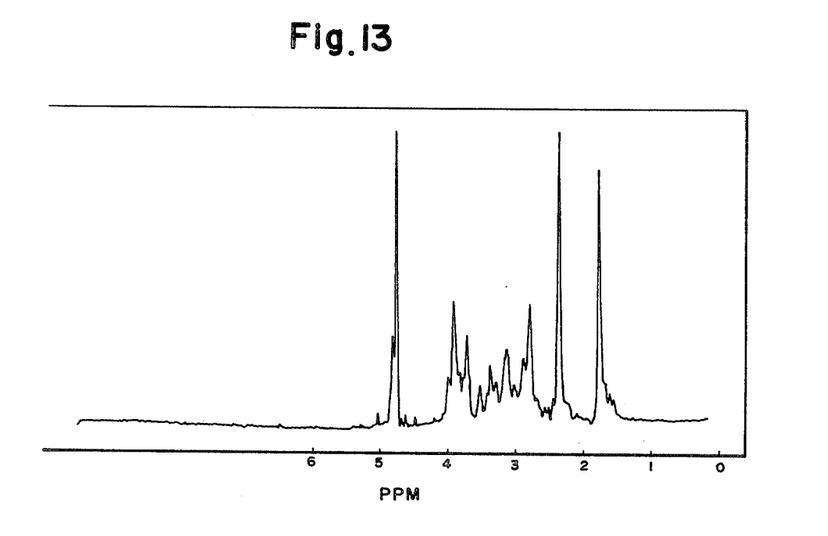

This substance is a blackish purple powdery substance which has no definite melting point and melts with blackening over a wide range beginning at around 150°–180° C. It shows as seen in FIG. 11 an ultraviolet absorption spectrum in methanol [illustrated with a solid line in FIG. 11] with three absorption maxima at 220 nm ($E_{1\ cm}^{1\%} = 375$), 275 nm (156) and 535 nm (28), the one in 0.05 N HCl- 95% methanol [illustrated with a dotted line in FIG. 11] with two absorption maxima at 266 nm ($E_{1\ cm}^{1\%} = 199$) and 410 nm (22) and the one in 0.05 N NaOH- 95% methanol [illustrated with a chain line in FIG. 11] with absorption maxima at 276 nm ($E_{1\ cm}^{1\%} = 148$) and 550 nm (34). It shows an infrared absorption spectrum (in Nujol) as shown in FIG. 12 with characteristic absorption bands at 3300, 1655, 1600, 1540, 1350, 1260, 1235, 1175, 1085, 1025, 1000, 905, 865, 835, 790 and 775 cm$^{-1}$ and also a nuclear magnetic resonance spectrum (in $D_2O$) as shown in FIG. 13. Analysis on C-13 nuclear magnetic resonance spectrum reveals that at least 19 carbon atoms are present within the molecule of Substance SF-1739 HP-5. Its molecular weight is estimated to be about 550 according to a vapor pressure method. It has the analytical composition: C, 60.93%; H, 7.05%; N, 8.41%; O, 23.61% (by difference). It is easily soluble in water and methanol, soluble in acetone and ethyl acetate and sparingly soluble in hexane. Its Rf values over a silica gel thin layer plate (available from E. Merck, West Germany) are 0.12 when developed with chloroform:methanol (9:1) and 0.12 when developed with ethyl acetate:methanol (3:2), while the corresponding values of Substance SF-1739 HP are 0.26 and 0.31, respectively. It is stable in dry state and in methanol, but slightly unstable in acidic methanol and less stable in alkaline methanol.

(III-b) Substance SF-1739 HP-3

(1) Physico-chemical properties

Figure 14:
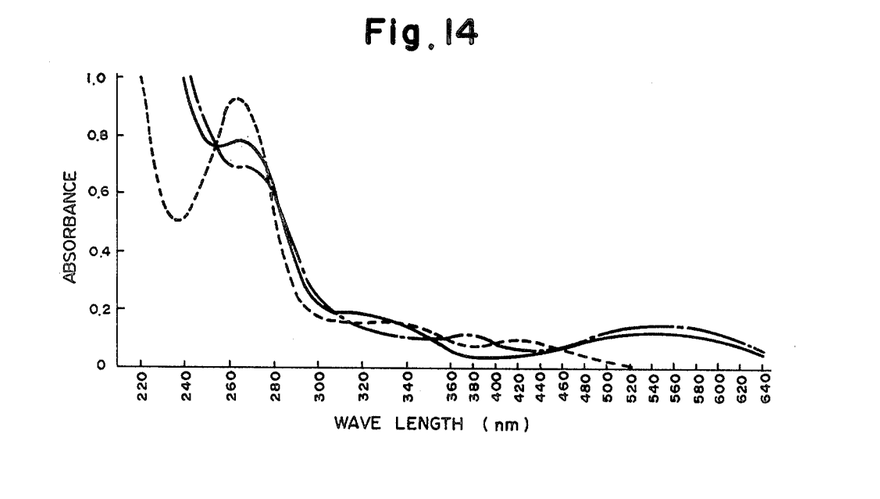
Figure 15:
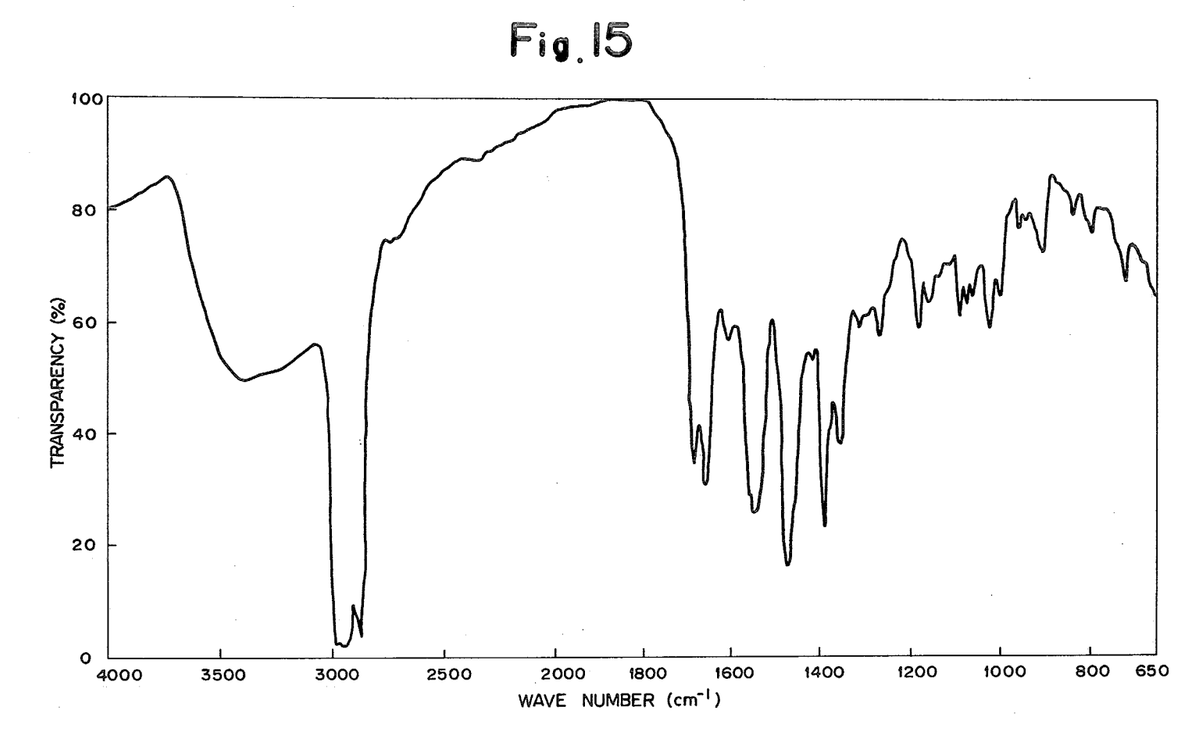
Figure 16:
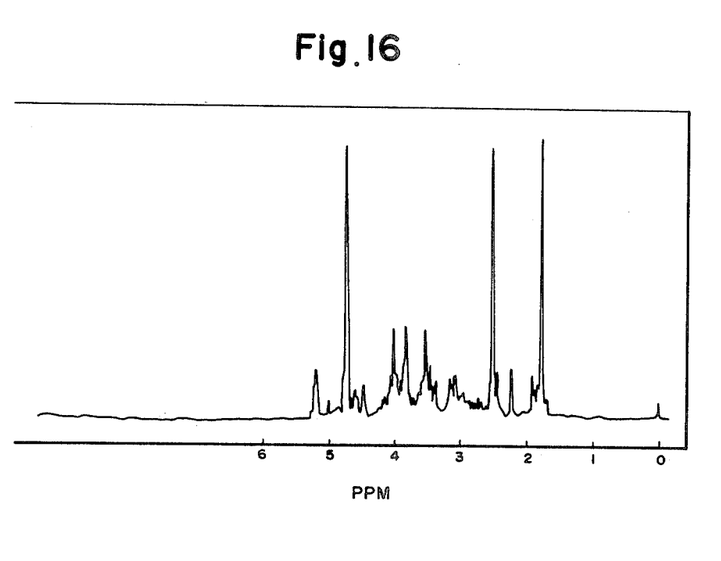

This substance is a blackish purple powdery substance which has no definite melting point and melts with blackening over a wide range beginning at around 130°–150° C. It shows as seen in FIG. 14 an ultraviolet absorption spectrum in methanol [illustrated with a solid line in FIG. 14] with four absorption maxima or inflection at 219 nm ($E_{1\ cm}^{1\%} = 890$), 267 nm (314), 330 nm (shoulder) and 543 nm (54), the one in 0.05 N HCl- 95% methanol [illustrated with a dotted line in FIG. 14] with three absorption maxima at 264 nm ($E_{1\ cm}^{1\%} = 372$), 325 nm (62), 420 nm (40), and the one in 0.05 N NaOH- 95% methanol [illustrated with a chain line in FIG. 14] with three maxima at 267 nm ($E_{1\ cm}^{1\%} = 276$), 375 nm (44) and 543 nm (64). It also shows an infrared absorption spectrum (in Nujol) as shown in FIG. 15 with characteristic absorption bands at 3355, 1680, 1655, 1600, 1545, 1350, 1310, 1265, 1180, 1155, 1085, 1070, 1055, 1020, 950, 955, 900, 835 and 790 cm$^{-1}$ and a nuclear magnetic resonance spectrum (in $D_2O$) as shown in FIG. 16. Its molecular weight is about 350 according to a vapor pressure method. It has the analytical composition: C, 64.13%; H, 5.01%; N, 9.25%; O, 21.61% (by difference). It is easily soluble in water and methanol, soluble in acetone and ethyl acetate and sparingly soluble in hexane. Its Rf values over a silica gel thin layer plate (available from E. Merck, West Germany) are 0.22 when developed with chloroform:methanol (9:1) and 0.39 when developed with ethyl acetate:methanol (3:2), while the corresponding values of Substance SF-1739 HP are 0.26 and 0.31, respectively. It is stable in neutral or acidic methanol, but less stable in alkaline methanol.

(III-c) Preparation of both Substances

These Substances can be prepared from natural yellow metabolites by treatment with an acid, said metabolites being produced in a cultured broth by cultivation of such actinomycetes as *Streptomyces griseoplanus* strain SF-1739 disclosed in the above-identified Japanese Published Unexamined Patent Application.

As the acid which may be employed for this treatment, there may be mentioned a mineral acid such as hydrochloric acid, hydrobromic acid, sulfuric acid and the like; and an organic acid such as trifluoroacetic acid, methanesulfonic acid, trifluoromethanesulfonic acid and the like. Reaction parameters may vary depending upon the sort and concentration of an acid to be employed and the solvent to be used. In case of the mineral acid, the treatment is desirably effected under cooling or at room temperature for 1 day to 1 week when a higher concentration of 5 to 10 N is applied or at room temperature or higher for one to several days when a lower concentration of not more than 5 N is applied. At an elevated temperature of above 80° C., by-products sometimes tend to be rather increased. The treatment may proceed rather rapidly in an aqueous solution, while it does more slowly in aqueous methanol. Conversion of the yellow metabolites to Substances SF-1739 HP-3 and SF-1739 HP-5 may take place under a pH range below 3.

After completion of the treatment, Substances SF-1739 HP-3 and SF-1739 HP-5 can be easily recovered from the reaction mixture by a conventional method, utilizing the above-recited physico-chemical properties of Substances SF-1739 HP-3 and SF-1739 HP-5. For instance, the reaction mixture can be neutralized with a base, e.g. sodium hydrogenecarbonate, potassium carbonate, and the like, concentrated to dryness and the residue is extracted with methanol, and then the extract is purified directly by a preparative silica gel thin layer chromatography. Alternatively, as less by-products are produced in this treatment, the reaction mixture can be concentrated, the residue is dissolved in methanol and the resulting solution is neutralized, and then passed through a column of Sephadex LH-20 (available from Pharmacia, Sweden), which can be subsequently developed with methanol or a mixed solvent of ethyl acetate and methanol to purify the desired products.

(III-d) For reference, the strain SF-1739 which can produce the starting yellow metabolites for this Preparation and the production of the yellow metabolites will be fully illustrated hereinbelow.

*Streptomyces griseoplanus* strain SF-1739 has been deposited under an accession No. 3002 with Technical Research Institute of Microbial Industry, Agency of Industrial Science & Technology, the Ministry of International Trade and Industry, Japan. This new strain has been deposited with the American Type Culture Collection as No. ATTC 31451 on Nov. 8, 1978. Morphological characteristics of the aforesaid strain No. 3002 is as follows:

(I) Morphology

Aerial mycelium abundantly grows on oatmeal-agar, yeastmalt-agar and the like with rich sporulation. Simple branches are observed, but cluster-like branches not seen. Loose open spiral is formed at the top of the aerial mycelium. Specific configuration like sclerotia is not observed. When observed under a microscope, spore surface is warty but partly spiny. Spores are elliptical to short cylindrical in shape and $0.6$–$0.8 \times 0.8$–$1.2\mu$ in size. Spore chains are generally in 10 or more spores per spore chain.

(II) Growth on various media (observed after cultivation at 28° C.)

| Medium | Browth* | Aerial mycelium | Soluble pigment |
|---|---|---|---|
| Sucrose . nitrate . agar | good, pale yellowish grey | grey | none |
| Glucose . asparagine . agar | scant, cream | poor, white | none |
| Glycerol . asparagine . agar | pale grey | grey | none |
| Starch . agar | good, pale yellowish grey-slightly olive grey | grey-olive grey | none |
| Oatmeal . agar | good, pale yellow grey | abundant, grey | none |
| Yeast . malt . agar | good, greyish yellow broun | abundant, dark grey | none |
| Tyrosine . agar | dark grey | olive grey | none |
| Nutrient . agar | pale yellow-greyish yellow | grey | none |

*on reverse

(III) Physiological properties

| | |
|---|---|
| Temperature range for growth: | 20°–40° C. on yeast . malt . agar medium |
| Gelatin liquefaction: | slow on cultivation at 20° C. over not less than 21 days |
| Hydrolysis of starch: | positive (strong at 28° C.) |
| Coagulation of skim milk: | positive (strong at 28° C. and 37° C.) |
| Petonization of skim milk: | positive (at 28° C. and 37° C.) |
| Melanin formation: | negative |

(IV) Carbon source utilization pattern (on PridhamGottlieb's agar medium at 28° C.

| | |
|---|---|
| D-glucose | + |
| D-fructose | + |
| D-xylose | + |
| D-mannitol | + |
| I-insitol | + |
| L-arabinose | + |
| Rhamnose | + |
| Sucrose | + |
| Raffinose | − |

Summarizing the above-recited properties, the strain SF-1739 belongs to the genus Streptomyces, is spiral at the top of aerial mycelium and has a warty spore surface. Growth on various media is grey to greyish yellow brown and aerial mycelium is grey. Melanin formation is not observed, nor soluble pigments seen.

Properties of the strain SF-1739 are most similar to those of *Streptomcyes griseoplanus* among the species of the genus Streptomyces. More specifically, both are perfectly common in spiral formation, warty spore surface, grey aerial mycelium, no melanin formation. In comparison of the strain SF-1739 with *Streptomyces griseoplanus* as described in ISP (International Streptomyces Project) [cf. International Journal of Systematic Bacteriology, 18, 124–126, (1968)], the strain given in ISP is different from the strain SF-1739 in poor growth on starch.agar, utilization of raffinose and no utilization of surose, L-inositol, D-mannitol and rhamnose, but the former is very similar to the latter in spore surface of being warty approximate to spiny.

From the foregoing, it seems reasonable that the strain SF-1739 belongs to the species, *Streptomyces griseoplanus*, since morephological properties are perfectly common each other and other principal properties are also common well. But the former is different from the strain given in ISP in carbon source utilization pattern and others. Therefore, the strain SF-1739 has been named *Streptomyces griseoplanus* strain SF-1739.

Although the preparation is explained herein mainly with regard to the strain SF-1739, it is well-known in the art that various properties of all microorganisms belonging to the genus Streptomyces are not definite, but microorganisms of the genus Streptomyces may be easily varied naturally and artificially. It is, accordingly, to be noted that all strains, which are capable of producing the starting antibiotic yellow metabolites and belongs to the genus Streptomyces including variants and mutants, are contemplated and usable herein.

Cultivation may be satisfactorily carried out in the same manner as commonly employed in the art for cultivation of any strain of the genus Streptomyces. As medium components, there may be employed any of well-known nutrient materials for the genus Streptomyces. For instance, as a carbon source, glucose, sucrose, starch, glycerol, corn syrup, molasses, soybean oil and the like may be used. As a nitrogen source, soybean meal, wheat embryo, meat extract, peptone, dry yeast, corn steep liquor, ammonium sulfate, sodium nitrate and the like may be employed. And further, such inorganic salts as calcium carbonate, sodium chloride, potassium chloride, phosphates, etc. may be added to a medium, if necessary. Also, a minor amount of any substance which can promote browth of the strain and accelerate the production of the antibiotic yellow metabolites. Cultivation may be effected according to liquid culture as usually applied in producing known antibiotic substances, most preferably in submerged culture. Cultivation temperature is desirably in the range of 25°–35°0 C., frequently around 28° C. Maximum production may be ordinarily accomplished in 2-6 days.

The yellow metabolites thus accumulated in a cultured broth is basic, semi-water soluble substances which are extremely unstable and have not successfully been isolated and identified.

In employing the aforesaid metabolites for treatment with an acid in order to produce Substances SF-1739 HP-3 and SF-1739 HP-5, a cultured broth containing the metabolites as such may be treated with an acid. Alternatively and more conveniently, the metabolities may be concentrated and subsequently subjected to the acid treatment.

For this preferable concentration of the metabolites, there may be employed any of well-known techniques commonly used for recovery of a basic, semi-water soluble natural product in the art. For instance, a cultured broth can be filtered, the filtrate can be made basic, saturated with sodium chloride, ammonium sulfate and the like, and then extracted with a water-immiscible organic solvent, e.g. n-butanol, ethyl acetate, butyl acetate, ether and the like. Also, the filtrate can be adsorbed on a cation exchange resin such as Amberlite IRC-50, CG-50, IR-120 or Dowex 50W and then elution can be done with an acid such as hydrochloric acid or sulfuric acid to obtain the metabolites in the concentrated state.

In order to obtain the desired metabolites in the more purified state, there may be used any combination of the above-mentioned extraction techniques and, alternatively, one may adopt adsorption with a resin, e.g. XAD-2, desorption, purification by column chromatography with Sephadex G-10. Carboxy methylcellulose and the like and/or scraping with a silica gel thin layer plate, etc.

Finally, the metabolites thus concentrated and fractionated may be preferably employed for the acid treatment to form Substances SF-1739 HP-3 and SF-1739 HP-5.

Biological activities of substance SF-1739 derivative of the present invention are set forth below.

I. Antimicrobial activity

Table 1 shows the minimal inhibitory concentration of the five substance SF-1739 derivatives of this invention.

Table 1.

Antimicrobial activity of substance SF-1739 derivatives

| Microbe | MIC (mcg./ml.) Substance SF-1739 | | | | |
|---|---|---|---|---|---|
| | HP | HP-C | HP-F | HP-5 | HP-3 |
| *Bacillus subtilis* | <0.09 | 0.78 | 1.56 | 12.5 | 3.1 |
| *Staphylococcus aureus* 209P | <0.09 | 3.125 | 1.25 | 50 | 3.1 |
| *Sarcina lutea* | <0.09 | <0.19 | 0.39 | 6.25 | 0.78 |
| *Escherichia coli* | 3.125 | >100 | >100 | >100 | >100 |
| *Escherichia coli* K-12R | 3.125 | >100 | >100 | >100 | >100 |
| *Klebsiella pneumonia* | 3.125 | 50 | >100 | >100 | >100 |
| *Pseudomonas aeruginosa* | 3.125 | >100 | >100 | >100 | >100 |
| *Proteus vulgaris* | 0.39 | 50 | 6.25 | >100 | >100 |

II. Antitumor activity

A: In vitro cytopathogenic activity

Table 2 shows the minimal cytopathogenic concentration of the five substance SF-1739 derivatives of this invention.

Table 2.

| Test substance | Minimal cytopathogenic concentration (mcg./ml.)* | | |
|---|---|---|---|
| | HeLa S3 | Hep. #2 | Sarcoma 180 |
| SF-1739 HP | 0.9 | <0.4 | <0.4 |
| SF-1739-HP-C | 0.9 | <0.4 | 0.9 |
| SF-1739 Hp-F | 0.9 | <0.4 | 0.9 |
| SF-1739 Hp-5 | 7.8 | 1.9 | 3.9 |
| SF-1739 Hp-3 | 3.9 | — | — |

*Evaluated after tissue culture for 48 hours.

B: In vivo carcinostatic effect in mice

Male CDF$_1$ strain mice (aged about 5 weeks, weighing 19±1 g., each group consisting of 3–5 animals) were intraperitoneally inoculated with P-388 leukemia cells at $10^6$/0.02 ml./mouse. Each test substance was dissolved in water at the indicated dose and intraperitoneally administered at 2–0.2 ml./day/mouse for 3 successive days after 24 hours from the inoculation. Thereafter, an increase in life span (ILS) was calculated. The results are summarized in Table 3.

Table 3.

| Test substance | Dose (mg./kg.) | ILS (%) |
|---|---|---|
| SF-1739 HP | 2 | 75.0 |
| | 1 | 43.3 |
| | 0.5 | 43.3 |
| | 0.25 | 45.0 |
| SF-1739 HP-C | 16 | 70.2 |
| | 8 | 53.8 |
| | 4 | 113.5 |
| | 2 | 61.5 |
| | 1 | 59.4 |
| SF-1739 HP-F | 16 | 47.1 |
| | 8 | 34.6 |
| SF-1739 HP-5 | 40 | 56.7 |
| | 20 | 51.9 |
| | 8 | 30.0 |
| | 4 | 25.0 |

III. Acute toxicity

Table 4 shows the acute toxicity (LD$_{50}$) of the five substance SF-1739 derivatives of this invention. When administered intravenously to mice.

Table 4.

| Substance | LD$_{50}$ (mg./kg.) |
|---|---|
| SF-1739 HP | 2 |
| SF-1739 HP-C | 20–25 |
| SF-1739 HP-F | >25 |
| SF-1739 HP-5 | >10 |
| SF-1739 HP-3 | >10 |
| SF-1739 | 0.45 |

In applying the present substance SF-1739 derivatives to the treatment of various types of tumors, they may be administered orally or parenterally in the form of a preparation usually admixed with a conventional solid or liquid pharmaceutically acceptable carrier or excipient. The solid preparation for oral administration may include a capsule, a tablet, a granule, a troche and the like and the topically applicable preparation may include a suppository, an ointment and the like. The liquid preparation may include a solution, a suspension, a syrup and the like and be applied orally, topically or by injection. Such preparations may be easily formed with conventional materials by any suitable techniques well-known to those skilled in the art. The amount of the active ingredient in the present preparation or composition as well as selection of the preparation form to be adopted may usually depend upon the type and severity of the disease to be treated, administration route, the body weight and age of a patient, activity and toxicity of the substance SF-1739 derivatives, and so on.

In case of an injectable preparation, it is desirable for adults to administer it subcutaneously, intramuscularly or, preferably, intravenously or intraarterially at a daily dose of 1–100 mg. continuously for several days or at a dose of 2–200 mg. every other day or every three days. It may sometimes be effective depending upon the type of tumor to inject the preparation directly to the tumor itself.

In case of oral administration, it is desirable for adults to administer the preparation in a single daily dose of 1–500 mg. every day or every other day.

In case of topical application, the active ingredient may be applied directly to an attacked or diseased part in the form of an admixture with a proper base so as to contain 1–20% of the active ingredient.

It also may be practiced to employ one or more of the present active derivatives either alone or in combination with other known antitumor agents and/or any immunoaccelerator.

In the case where the present substance SF-1739 derivative is to be employed as an antimicrobial agent, especially as an antibacterial agent, it may be also administered orally or parenterally in the form of a solid or liquid preparation commonly employed in the art for other known antibacterial agents or antibiotics. As the preparation for oral administration, there may be, for example, a capsule, a tablet, a powder, a granule, a solution, a suspension or a syrup. For topical application, there may be mentioned, for example, a suppository, an ointment and the like. As the preparation for parenteral administration, there may be an injectable solution or suspension and the preparation may be given subcutaneously, intramuscularly or intravenously. The amount of the active derivative to be administered may vary depending upon the type and severity of a disease, the body weight and age of a patient, activity and toxicity of the substance SF-1739 derivatives and other factors, but the active derivative may be usually employed for adults at a daily dose of 1–500mg. for oral administration in a single dosage form or several divided forms or at a single dose of 1–100 mg. for parenteral, e.g., intramuscular or intravenous administration. A higher or lower dose may be selected and used by a physician with special attention being paid to the severity of a disease, physical conditions of a patient and any adverse effect.

The substance SF-1739 derivatives of this invention may be administered either alone, as a mixture thereof or in combination with any of other known antimicrobial agents such as various antibiotics and the like.

The following examples are given for the purpose of illustrating this invention more fully.

EXAMPLE 1

Preparation of Substance SF-1739 HP

A solution of 6 mg. of SF-1739 hydrochloride in 3 ml. of 5 N hydrochloric acid was left at room temperature for 1 week. The solution was then neutralized with solid sodium hydrogencarbonate and the neutralized solution was concentrated to dryness under reduced pressure. The residue was dissolved in a small amount of methanol, insolubles were filtered off and the filtrate was concentrated. The residue was placed on a preparative silica gel thin layer chromatography plate (2×100×100 mm., available from E. Merck, West Germany), which was then developed with a mixed solvent of chloroform and methanol (9:1). A purple band with Rf of 0.45 was cut from the plate and extracted with methanol.

The extract was concentrated to dryness. The residue was redissolved in a mixed solvent of methanol and acetone (2:1) and insolubles were filtered off. The filtrate was concentrated to dryness to leave 3.3 mg. of Substance SF-1739 HP.

EXAMPLE 2

Preparation of Substance SF-1739 HP-C

To a solution of 71 mg. of Substance SF-1739 HP in 5 ml. of water were added 144 mg. of sodium cyanide and the resulting mixture was left at room temperature for 30 minutes. Thereafter, it was concentrated to dryness under reduced pressure below 35° C. with addition of n-butanol. The residue was dissolved in a small amount of methanol, insolubles were filtered off and the filtrate was concentrated. The residue was placed on a preparative silica gel thin layer chromatography plate (2×100×100 mm., available from E. Merck, West Germany), which was then developed with a mixed solvent of ethyl acetate and methanol (3:2). A purple band with Rf of 0.70 was scraped off and extracted with methanol. The extract was concentrated to dryness and the residue was redissolved in a mixed solvent of methanol and acetone (2:1), insolubles were filtered off and then the filtrate was concentrated to dryness to afford 35 mg. of Substance SF-1739 HP-C.

EXAMPLE 3

Preparation of Substance SF-1739 HP-F

A solution of 35 mg. of Substance SF-1739 HP in 1.5 ml. of formamide was left at room temperature for 5 minutes. The reaction mixture was then concentrated to dryness under reduced pressure below 50° C. The residue was dissolved in a small amount of methanol and the resulting solution was placed on a preparative silica gel thin layer chromatography plate (2×100×100 mm., available from E. Merck, West Germany), which was then developed with a mixed solvent of ethyl acetate and methanol (3:2). A purple band with Rf of 0.53 was scraped off and extracted with methanol. The extract was concentrated to dryness, the residue was redissolved in a mixed solvent of methanol and acetone (2:1), insolubles were filtered off and then the filtrate was concentrated to dryness to give 25 mg. of Substance SF-1739 HP-F.

EXAMPLE 4

Preparation of Substance SF-1739 HP-C

To a solution of 73 mg. of Substance SF-1739 HP in 2 ml. of methanol were added 72 mg. of potassium cyanide and the resulting mixture was stirred at room temperature for 5 minutes. The reaction mixture was placed on a preparative silica gel thin layer chromatography plate (2×100×100 mm., available from E. Merck, West Germany), which was then developed with a mixed solvent of ethyl acetate and methanol (3:2). A purple band with Rf of 0.70 was scraped off and extracted with methanol. The extract was concentrated to dryness, the residue was redissolved in a mixed solvent of methanol and acetone (2:1), insolubles were filtered off and then the filtrate was concentrated to dryness to give 50 mg. of Substance SF-1739 HP-C.

EXAMPLE 5

Preparation of substances SF-1739 HP-3, SF-1739 HP-5 and SF-1739 HP

Spores of *Streptomyces griseoplanus* strain SF-1739 (Accession No. 3002 with Technical Research Institute of Microbial Industry) were innoculated on 1.6 l. of a liquid medium consisting of starch 1.0% and soy bean meal 3.0% (pH 7.0), and shaking culture was effected at 28° C. for 30 hours by the use of 16 Sakaguchi flasks to produce a seed culture.

The so obtained seed culture was innoculated on 70 l. of a liquid medium consisting of starch syrup 3.0%, soy bean meal 2.0%, beef extract 1.0%, wheat embryo 1.0% and sodium chloride 0.3% (pH 6.6), and shaking culture with aeration was effected at 28° C. for 90 hours by the use of 2 jar fermenters, each having a 50 l. volume.

The cultured broth was adjusted to pH 3-4 with 6 N hydrochloric acid and filtered with a filter acid, Hyflo Super Cel. The filtrate (about 47 l.) was adjusted to pH 6 with 3 N sodium hydroxide and passed through a column of about 4 l. of an ion exchange resin, Amberlite IRC-50 (H$^+$) to adsorb antibiotic metabolites. The column was thoroughly washed with water and eluated with 0.2 N aqueous hydrochloric acid. Active fraction of about 4.5 l. was saturated with sodium chloride, adjusted to pH 8.0 with sodium hydroxide and then extracted twice with each 1 l. portion of ethyl acetate under cooling. The ethyl acetate extract was re-extracted with 200 ml. of 0.05 N aqueous hydrochloric acid. The resulting aqueous solution (pH 2.0) was concentrated to dryness under reduced pressure to leave 1.68 g. of antibiotic metabolites as crude powder. The crude powder was dissolved in 20 ml. of 5 N hydrochloric acid, left at room temperature for 1 week and then concentrated again to dryness under reduced pressure. The residue was dissolved in 20 ml. of methanol and the resulting yellowish-red solution was neutralized with solid sodium hydrogencarbonate until it became purple. Insolubles were filtered off, the filtrate was concentrated, and then the residue was placed on 7 preparative silica gel thin layer chromatography plates (2×100×100 mm., available from E. Merck, West Germany), which were then developed with a mixed solvent of ethyl acetate and methanol (3:2). A purple band with Rf of 0.12 was scraped off from each plate and extracted with methanol. The combined extract was concentrated to dryness to give Substance SF-1739 HP-5 as crude powder. The crude powder was dissolved in a small amount of methanol and placed on three preparative silica gel thin layer chromatography plates, which were then developed with a mixed solvent of chloroform and methanol (9:1). Purple bands with Rf of 0.12 were scraped off, extracted with methanol and the extract was concentrated to dryness. The residue was dissolved in a mixed solvent of methanol and acetone (3:1), insolubles were filtered off and the filtrate was concentrated to dryness to yield 153 mg. of Substance SF-1739 HP-5.

From the first silica gel thin layer chromatography plates were scraped off purple bands with Rf of 0.39 and extracted with methanol. The extract was concentrated to dryness, the residue was dissolved in a small amount of methanol and placed on a preparative silica gel thin layer chromatography plate (2×100×100 mm., available from E. Merck, West Germany), which was then developed with a mixed solvent of chloroform and methanol (9:1). A purple band with Rf of 0.22 was scraped off and extracted with methanol. The extract was concentrated to dryness, the residue was dissolved in a mixed solvent of methanol and acetone (2:1), insolubles were filtered off and then the filtrate was concentrated to dryness to afford 27 mg. of Substance SF-1739 HP-3.

From the first silica gel thin layer chromatography plates were scraped off purple bands with Rf of 0.31 and extracted with methanol. The extract was concentrated to dryness, the residue was dissolved in a small amount of methanol and placed on two preparative silica gel thin layer chromatography plates (2×100×100 mm., available from E. Merck, West Germany), which were then developed with a mixed solvent of chloroform and methanol (9:1). Purple bands with Rf of 0.26 were scraped off and extracted with methanol. The extract was concentrated to dryness, the residue was dissolved in a mixed solvent of methanol and acetone (2:1), insolubles were filtered off and then the filtrate was concentrated to dryness to afford 99 mg. of Substance SF-1739 HP.

We claim:

1. A substance SF-1739 HP having the following physico-chemical properties:
   (1) blackish purple substance;
   (2) ultraviolet absorption spectrum as shown in FIG. 1;
   (3) infrared absorption spectrum as shown in FIG. 2 with characteristic absorption bands at 3350, 1655, 1600, 1540, 1355, 1265, 1235, 1180, 1120, 1080, 1020, 1000, 965, 945, 920, 910, 865, 830, 790 and 750 cm$^{-1}$;
   (4) nuclear magnetic resonance spectrum as shown in FIG. 3;
   (5) optical rotatory dispersion curve as shown in FIG. 4;
   (6) elementary analysis
      found: C, 62.19%; H, 6.95%; N, 8.50%: O, 22.36% (by difference);
   (7) solubility
      easily soluble in water and methanol, soluble in ethyl acetate and sparingly soluble in hexane;
   (8) chromatography
      by a thin layer chromatography on silica gel, Rf values=0.45 (chloroform:methanol=9:1) or 0.23 (n-butanol:methanol:0.1 N hydrochloric acid=4:2:1).

2. A substance SF-1739 HP-C having the following physico-chemical properties:
   (1) blackish purple substance;
   (2) ultraviolet absorption spectrum as shown in FIG. 5;
   (3) infrared absorption spectrum as shown in FIG. 6 with characteristic absorption bands at 3350, 1660, 1600, 1535, 1355, 1265, 1235, 1200, 1175, 1140, 1120, 1080, 1060, 1000, 940, 910, 880, 835 and 795 cm$^{-1}$;
   (4) optical rotatory dispersion curve as shown in FIG. 7;
   (5) nuclear magnetic resonance spectrum as shown in FIG. 8;
   (6) elementary analysis
      found: C, 59.58%; H, 6.14%; N, 12.63%; O, 21.65% (by difference);
   (7) solubility
      easily soluble in water and methanol, soluble in acetone and ethyl acetate and sparingly soluble in hexane;
   (8) chromatography
      by a thin layer chromatography on silica gel, Rf values=0.40 (chloroform:methanol=9:1) and 0.70 (ethyl acetate:methanol=3:2).

3. A substance SF-1739 HP-F having the following physico-chemical properties:
   (1) blackish purple substance;
   (2) ultraviolet absorption spectrum as shown in FIG. 9;
   (3) infrared absorption spectrum as shown in FIG. 10 with characteristic absorption bands at 3300, 1660, 1530, 1350, 1310, 1265, 1235, 1205, 1175, 1125, 1085, 1025, 1000, 940, 920, 830 and 795 cm$^{-1}$;
   (4) elementary analysis found: C, 57.26%; H, 6.33%; N, 12.14%; O, 24.27% (by difference);
(5) solubility
  easily soluble in water and methanol, soluble in acetone and ethyl acetate and sparingly soluble in hexane;
(6) chromatography
  by a thin layer chromatography on silica gel, Rf values=0.28 (chloroform:methanol=9:1) and 0.53 (ethyl acetate:methanol=3:2).

4. A substance SF-1739 HP-5 having the following physico-chemical properties:
(1) blackish purple substance;
(2) ultraviolet absorption spectrum as shown in FIG. 11;
(3) infrared absorption spectrum as shown in FIG. 12 with characteristic absorption bands at 3300, 1655, 1600, 1540, 1350, 1260, 1235, 1175, 1085, 1025, 1000, 905, 865, 835, 790 and 775 cm$^{-1}$;
(4) nuclear magnetic resonance spectrum as shown in FIG. 13;
(5) elementary analysis
  found: C, 60.93%; H, 7.05%; N, 8.41%; O, 23.61% (by difference);
(6) solubility
  easily soluble in water and methanol, soluble in ethyl acetate and acetone and sparingly soluble in hexane;
(7) chromatography
  by a thin layer chromatography on silica gel, Rf values=0.12 (chloroform:methanol=9:1) and 0.12 (ethyl acetate:methanol=3:2).

5. A substance SF-1739 HP-3 having the following physico-chemical properties:
(1) blackish purple substance;
(2) ultraviolet absorption spectrum as shown in FIG. 14;
(3) infrared absorption spectrum as shown in FIG. 15 with characteristic absorption bands as 3355, 1680, 1655, 1600, 1545, 1350, 1310, 1265, 1180, 1155, 1085, 1070, 1055, 1020, 955, 950, 900, 835 and 790 cm$^{-1}$;
(4) nuclear magnetic resonance spectrum as shown in FIG. 16;
(5) elementary analysis
  found: C, 64.13%; H, 5.01%; N, 9.25%; O, 21.61% (by difference);
(6) solubility
  easily soluble in water and methanol, soluble in acetone and ethyl acetate and sparingly soluble in hexane;
(7) chromatography
  by a thin layer chromatography on silica gel, Rf values=0.22 (chloroform:methanol=9:1) and 0.39 (ethyl acetate:methanol=3:2).

6. An antibacterial composition which comprises an antibacterially effective amount of at least one substance selected from the group consisting of Substance SF-1739 HP, Substance SF-1739 HP-C, Substance SF-1739 HP-F, Substance SF-1739 HP-5 and Substance SF-1739 HP-3, and a pharmaceutically acceptable carrier, said Substance SF-1739 HP having the following physico-chemical properties:
(1) blackish purple substance;
(2) ultraviolet absorption spectrum as shown in FIG. 1;
(3) infrared absorption spectrum as shown in FIG. 2 with characteristic absorption bands at 3350, 1655, 1600, 1540, 1355, 1265, 1235, 1180, 1120, 1080, 1020, 1000, 965, 945, 920, 910, 865, 830, 790 and 750 cm$^{-1}$;
(4) nuclear magnetic resonance spectrum as shown in FIG. 3;
(5) optical rotatory dispersion curve as shown in FIG. 4;
(6) elementary analysis
  found: C, 62.19%; H, 6.95%; N, 8.50%; O, 22.36% (by difference);
(7) solubility
  easily soluble in water and methanol, soluble in ethyl acetate and sparingly soluble in hexane;
(8) chromatography
  by a thin layer chromatography on silica gel, Rf values=0.45 (chloroform:methanol=9:1) or 0.23 (n-butanol:methanol:0.1 N hydrochloric acid=4:2:1);

said Substance SF-1739 HP-C having the following physico-chemical properties:
(1) blackish purple substance;
(2) ultraviolet absorption spectrum as shown in FIG. 5;
(3) infrared absorption spectrum as shown in FIG. 6 with characteristic absorption bands at 3350, 1660, 1600, 1535, 1355, 1265, 1235, 1200, 1175, 1140, 1120, 1080, 1060, 1000, 940, 910, 880, 835 and 795 cm$^{-1}$;
(4) optical rotatory dispersion curve as shown in FIG. 7;
(5) nuclear magnetic resonance spectrum as shown in FIG. 8;
(6) elementary analysis
  found: C, 59.58%, H, 6.14%; N, 12.63%; O, 21.65% (by difference);
(7) solubility
  easily soluble in water and methanol, soluble in acetone and ethyl acetate and sparingly soluble in hexane;
(8) chromatography
  by a thin layer chromatography on silica gel, Rf values=0.40 (chloroform:methanol=9:1) and 0.70 (ethyl acetate:methanol=3:2);

said Substance SF-1739 HP-F having the following physico-chemical properties:
(1) blackish purple substance;
(2) ultraviolet absorption spectrum as shown in FIG. 9;
(3) infrared absorption spectrum as shown in FIG. 10 with characteristic absorption bands at 3300, 1660, 1530, 1350, 1310, 1265, 1235, 1205, 1175, 1125, 1085, 1025, 1000, 940, 920, 830 and 795 cm$^{-1}$;
(4) elementary analysis
  found: C, 57.26%; H, 6.33%; N, 12.14%; O, 24.27% (by difference);
(5) solubility
  easily soluble in water and methanol, soluble in acetone and ethyl acetate and sparingly soluble in hexane;
(6) chromatography
  by a thin layer chromatography on silica gel, Rf balues=0.28 (chloroform:methanol=9:1) and 0.53 (ethyl acetate:methanol=3:2);

said Substance SF-1739 HP-5 having the following physico-chemical properties:
(1) blackish purple substance;
(2) ultraviolet absorption spectrum as shown in FIG. 11;

(3) infrared absorption spectrum as shown in FIG. 12 with characteristic absorption bands at 3300, 1655, 1600, 1540, 1350, 1260, 1235, 1175, 1085, 1025, 1000, 905, 865, 835, 790 and 775 cm$^{-1}$;

(4) nuclear magnetic resonance spectrum as shown in FIG. 13;

(5) elementary analysis
found: C, 60.93%; H, 7.05%; N, 8.41%; O, 23.61% (by difference);

(6) solubility
easily soluble in water and methanol, soluble in ethyl acetate and acetone and sparingly soluble in hexane;

(7) chromatography
by a thin layer chromatography on silica gel, Rf values=0.12 (chloroform:methanol=9:1) and 0.12 (ethyl acetate:methanol=3:2); and said Substance SF-1739 HP-3 having the following physico-chemical properties:

(1) blackish purple substance;

(2) ultraviolet absorption spectrum as shown in FIG. 14;

(3) infrared absorption spectrum as shown in FIG. 15 with characteristic absorption bands at 3355, 1680, 1655, 1600, 1545, 1350, 1310, 1265, 1180, 1155, 1085, 1070, 1055, 1020, 955, 950, 900, 835 and 790 cm$^{-1}$;

(4) nuclear magnetic resonance spectrum as shown in FIG. 16;

(5) elementary analysis
found: C, 64.13%; H, 5.01%; N, 9.25%; O, 21.61% (by difference);

(6) solubility
easily soluble in water and methanol, soluble in acetone and ethyl acetate and sparingly soluble in hexane;

(7) chromatography
by a thin layer chromatography on silica gel, Rf values=0.22 (chloroform:methanol=9:1) and 0.39 (ethyl acetate:methanol=3:2).

7. The antibacterial composition of claim 6, wherein said antibiotic substance is said SF-1739 HP.

8. The antibacterial composition of claim 6, wherein said antibiotic substance is said SF-1739 HP-C.

9. The antibacterial composition of claim 6, wherein said antibiotic substance is said SF-1739 HP-F.

10. The antibacterial composition of claim 6, wherein said antibiotic substance is said SF-1739 HP-5.

11. The antibacterial composition of claim 6, wherein said antibiotic substance is said SF-1739 HP-3.

* * * * *